US00PP21232P2

(12) United States Plant Patent
Bernuetz

(10) Patent No.: US PP21,232 P2
(45) Date of Patent: Aug. 24, 2010

(54) ***XEROCHRYSUM* PLANT NAMED 'BONDREYEL'**

(50) Latin Name: *Xerochrysum bracteatum*
Varietal Denomination: Bondreyel

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 12/386,658

(22) Filed: Apr. 20, 2009

(51) Int. Cl.
*A01H 5/00* (2006.01)

(52) U.S. Cl. ..... Plt./359

(58) Field of Classification Search ..... Plt./359, Plt./263.1

See application file for complete search history.

*Primary Examiner*—Annette H Para
(74) *Attorney, Agent, or Firm*—C.A. Whealy

(57) ABSTRACT

A new and distinct cultivar of *Xerochrysum* plant named 'Bondreyel', characterized by its compact, upright, mounding and uniform plant habit; freely flowering habit; inflorescences with bright yellow-colored involucral bracts; and strong peduncles that hold the inflorescences above the foliar plane.

1 Drawing Sheet

Botanical designation: *Xerochrysum bracteatum.*
Cultivar denomination: 'Bondreyel'.

BACKGROUND OF THE INVENTION

The present invention relates to a new and distinct cultivar of *Xerochrysum* plant, botanically known as *Xerochrysum bracteatum*, and hereinafter referred to by the name 'Bondreyel'. The genus *Xerochrysum* was formerly classified within the genus *Bracteantha*, that is, the specific epithet, *Xerochrysum bracteatum*, was previously known as *Bracteantha bracteata.*

The new *Xerochrysum* plant is a product of a planned breeding program conducted by the Inventor in Yellow Rock, New South Wales, Australia. The objective of the breeding program is to create and develop new compact *Xerochrysum* cultivars with uniformly mounded plant habit, freely flowering habit and attractive inflorescences.

The new *Xerochrysum* plant originated from an open-pollination by the Inventor in 2000 of the *Bracteantha bracteata* 'Rose Pink', disclosed in U.S. Plant Pat. No. 13,923, as the female, or seed, parent with an unknown selection of *Xerochrysum bracteatum*, not patented, as the male, or pollen, parent. The new *Xerochrysum* was discovered and selected by the Inventor as a single flowering plant within the progeny of the stated open-pollination in a controlled greenhouse environment in Yellow Rock, New South Wales, Australia in March, 2001.

Asexual reproduction of the new *Xerochrysum* plant by terminal cuttings in a controlled greenhouse environment in Yellow Rock, New South Wales, Australia since April, 2001, has shown that the unique features of this new *Xerochrysum* plant are stable and reproduced true to type in successive generations.

SUMMARY OF THE INVENTION

Plants of the new *Xerochrysum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Bondreyel'. These characteristics in combination distinguish 'Bondreyel' as a new and distinct cultivar of *Xerochrysum:*

1. Compact, upright, mounding and uniform plant habit.
2. Freely flowering habit.
3. Inflorescences with bright yellow-colored involucral bracts.
4. Strong peduncles that hold the inflorescences above the foliar plane.

In side-by-side comparisons conducted in Yellow Rock, New South Wales, Australia, plants of the new *Xerochrysum* differed from plants of the female parent, 'Rose Pink', primarily in involucral bract color as plants of 'Rose Pink' have dark pink-colored involucral bracts.

Plants of the new *Xerochrysum* can be compared to plants of the *Bracteantha bracteata* 'OHB003790', disclosed in U.S. Plant Pat. No. 15,629. In side-by-side comparisons conducted in Yellow Rock, New South Wales, Australia, plants of the new Xerochrysum differed from plants of 'OHB003790' in the following characteristics:

1. Plants of the new *Xerochrysum* were more compact than plants of 'OHB003790'.
2. Plants of the new *Xerochrysum* had smaller leaves than plants of 'OHB003790'.
3. Plants of the new *Xerochrysum* had smaller inflorescences than plants of 'OHB003790'.
4. Inflorescences of plants of the new *Xerochrysum* had more involucral bracts and disc florets than inflorescences of plants of 'OHB003790'.

BRIEF DESCRIPTION OF THE PHOTOGRAPHS

The accompanying photographs illustrate the overall appearance of the new *Xerochrysum* plant.

These photographs show the colors as true as it is reasonably possible to obtain in colored reproductions of this type.

Colors in the photographs may differ slightly from the color values cited in the detailed botanical description which accurately describe the colors of the new *Xerochrysum* plant.

The photograph at the top of the sheet comprises a side perspective view of a typical flowering plant of 'Bondreyel' grown in a container.

The photograph at the bottom of the sheet comprises a close-up view of typical inflorescences of 'Bondreyel'.

DETAILED BOTANICAL DESCRIPTION

The aforementioned photographs and following observations and measurements describe plants grown in Higashiomi, Shiga, Japan during the spring in a polyethylene-covered greenhouse and under conditions and practices which approximate those generally used in commercial *Xerochrysum* production. During the production of the plants, day temperatures averaged 23° C. and night averaged 13° C. Measurements and numerical values represent averages for typical flowering plants. Plants were about four months old when the photographs and description were taken. In the following description, color references are made to The Royal Horticultural Society Colour Chart, 2001 Edition, except where general terms of ordinary dictionary significance are used.

Botanical classification: *Xerochrysum bracteatum* 'Bondreyer'.

Parentage:

*Female, or seed, parent.*—*Bracteantha bracteata* 'Rose Pink', disclosed in U.S. Plant Pat. No. 13,923.

*Male, or pollen, parent.*—Unknown selection of *Xerochrysum bracteatum*, not patented.

Propagation:

*Type.*—Terminal vegetative cuttings.

*Time to initiate roots.*—About six to nine days at 20° C. to 25° C.

*Time to produce a rooted cutting.*—About three weeks at 20° C. to 25° C.

*Root description.*—Fibrous; white in color.

*Rooting habit.*—Freely branching; moderately dense.

Plant description:

*Plant form/growth habit.*—Compact, upright, mounding and uniform plant habit with inflorescences held above the foliage on strong peduncles; vigorous growth habit.

*Plant height.*—About 16.1 cm.

*Plant diameter or spread.*—About 29.7 cm.

*Lateral branches.*—Quantity per plant: Freely branching habit with about eight lateral branches per plant. Length: About 14 cm. Diameter: About 4 mm. Internode length: About 9.6 mm. Aspect: Upright. Strength: Strong. Texture: Pubescent. Color: Close to 144A.

*Foliage description.*—Arrangement: Alternate, simple; sessile. Length: About 5.6 cm. Width: About 8 mm. Shape: Lanceolate. Apex: Acute. Base: Cuneate. Margin: Entire. Texture, upper and lower surfaces: Pubescent. Venation pattern: Pinnate; reticulate. Color: Developing leaves, upper surface: Close to 137B. Developing leaves, lower surface: Close to 137C. Fully expanded leaves, upper surface: Close to 137A; venation, close to 144C. Fully expanded leaves, lower surface: Close to 137C; venation, close to 144C.

Inflorescence description:

*Appearance.*—Double-type inflorescence form with lanceolate involucral bracts; involucral bracts and disc florets developing acropetally on a capitulum; inflorescences positioned above the foliar plane on strong peduncles; inflorescences face mostly upright.

*Flowering habit.*—Freely flowering habit; about nine inflorescences per plant.

*Fragrance.*—None detected.

*Time to flower.*—In Japan, plants begin to flower about 14 weeks after planting and in the garden, plant flower continuously from the spring through autumn.

*Post-production longevity.*—Inflorescences maintain good substance for about 18 days on the plant; inflorescences persistent.

*Inflorescence bud.*—Height: About 1 cm. Diameter: About 5 mm. Shape: Ovoid. Color: Close to 165B.

*Inflorescence size.*—Diameter: About 4.8 cm. Depth (height): About 2.3 cm. Disc diameter: About 1.7 cm.

*Involucral bracts.*—Shape: Lanceolate. Length: About 1.1 cm to 1.7 cm. Width: About 1.2 mm to 5.4 mm. Apex: Acute. Base: Truncate. Margin: Entire. Texture: Smooth, glabrous; papery. Orientation: Initially upright becoming horizontal with development. Number of involucral bracts per inflorescence: About 370 in about 15 to 20 whorls. Color: When opening and fully opened, upper surface: Close to 9A; towards the apex, close to 23A. When opening and fully opened, lower surface: Close to 9A overlain with close to 67A.

*Disc florets.*—Arrangement: Massed in the center of the receptacle. Shape: Tubular; apex dentate, five-pointed. Length: About 1.1 cm. Diameter: About 2.9 mm. Number of disc florets per inflorescence: About 680. Color: Immature: Close to 2A. Mature: Close to 23A.

*Peduncles.*—Length: About 6.3 cm. Diameter: About 2.2 mm. Strength: Strong. Aspect: Upright. Texture: Tomentose. Color: Close to 144A.

*Reproductive organs* (*present on disc florets only*).—Androecium: Quantity per disc floret: About five. Stamen length: About 6.8 mm. Anther shape: Lanceolate. Anther color: Close to 23A. Pollen amount: Scarce. Pollen color: Close to 23A. Gynoecium: Pistil length: About 1.1 cm. Stigma shape: Bi-parted. Stigma color: Close to 23A. Style color: Close to 155A. Ovary color: Close to 155A.

*Seed/fruit.*—Seed and fruit production has not been observed.

Disease/pest resistance: Plants of the new *Xerochrysum* have not been shown to be resistant to pathogens and pests common to *Xerochrysum*.

Temperature tolerance: Plants of the new *Xerochrysum* have been observed to tolerate temperatures ranging from about 0° C. to about 35° C.

It is claimed:

1. A new and distinct *Xerochrysum* plant named 'Bondreyel' as illustrated and described.

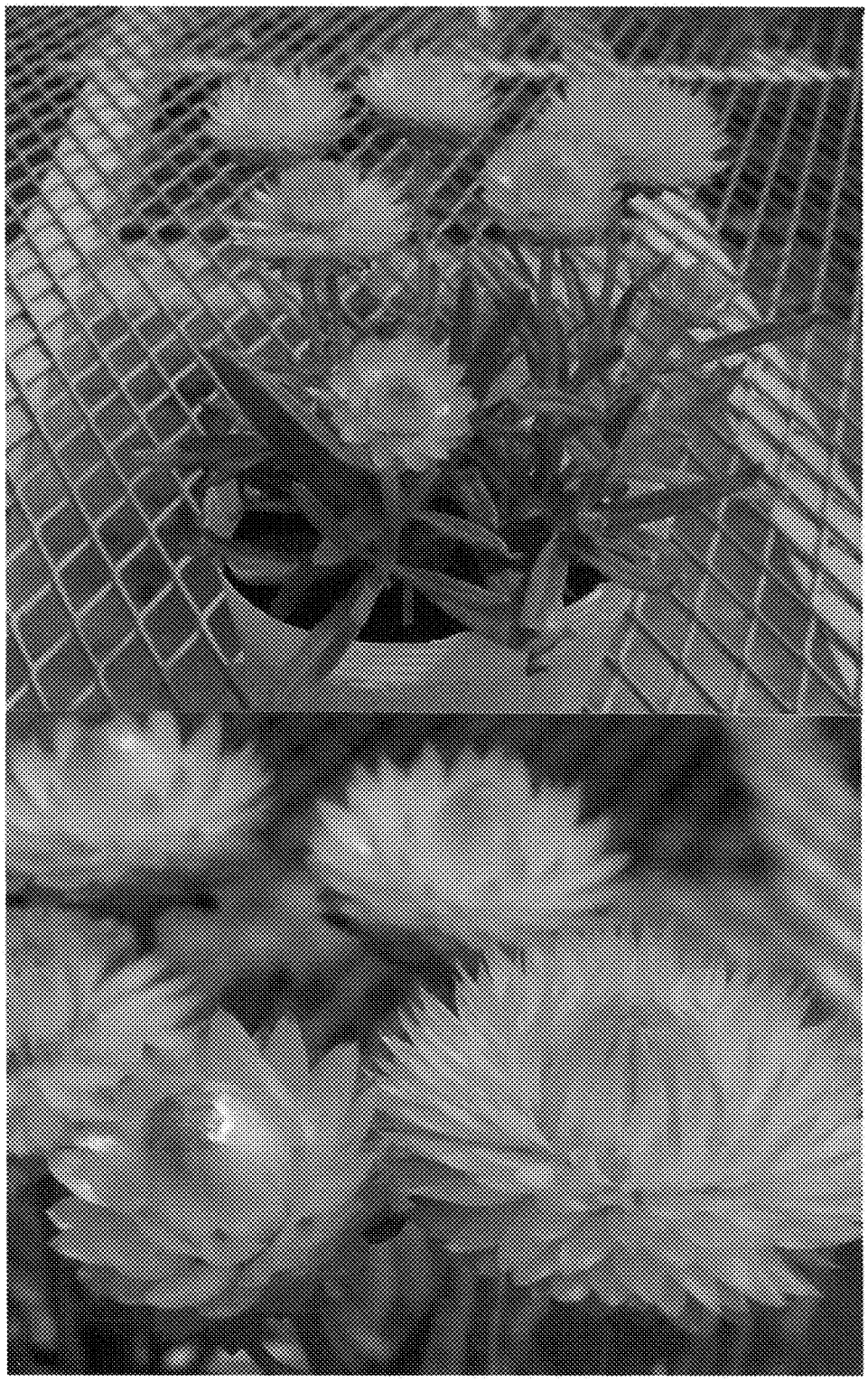

* * * * *